(12) United States Patent
Yanof et al.

(10) Patent No.: US 7,182,083 B2
(45) Date of Patent: Feb. 27, 2007

(54) CT INTEGRATED RESPIRATORY MONITOR

(75) Inventors: Jeffrey H. Yanof, Solon, OH (US); Peter C. Johnson, South Euclid, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/280,626

(22) Filed: Oct. 25, 2002

(65) Prior Publication Data

US 2003/0188757 A1 Oct. 9, 2003

Related U.S. Application Data

(60) Provisional application No. 60/369,485, filed on Apr. 3, 2002.

(51) Int. Cl.
*A61M 16/00* (2006.01)
*A62B 7/00* (2006.01)
*F16K 31/02* (2006.01)

(52) U.S. Cl. .................. 128/204.23; 128/916; 600/428

(58) Field of Classification Search .......... 128/204.23, 128/898, 916; 600/428, 534, 443
See application file for complete search history.

(56) References Cited

U.S. PATENT DOCUMENTS

| | | | |
|---|---|---|---|
| 4,694,836 A | | 9/1987 | Buikman et al. |
| 5,178,151 A | * | 1/1993 | Sackner ...................... 600/485 |
| 5,363,844 A | | 11/1994 | Riederer et al. |
| 5,482,042 A | * | 1/1996 | Fujita ......................... 600/428 |
| 5,830,143 A | * | 11/1998 | Mistretta et al. ............ 600/420 |
| 6,014,473 A | * | 1/2000 | Hossack et al. ............ 382/294 |
| 6,076,005 A | * | 6/2000 | Sontag et al. ............... 600/413 |
| 6,094,591 A | * | 7/2000 | Foltz et al. .................. 600/419 |
| 6,118,847 A | * | 9/2000 | Hernandez-Guerra et al. ............................ 378/65 |
| 6,139,500 A | * | 10/2000 | Clark ......................... 600/443 |
| 6,144,201 A | * | 11/2000 | Miyazaki .................... 324/306 |

(Continued)

FOREIGN PATENT DOCUMENTS

EP 0 072 601 B1 7/1986

(Continued)

*Primary Examiner*—Michael J. Hayes
*Assistant Examiner*—Michael G. Mendoza
(74) *Attorney, Agent, or Firm*—Fay, Sharpe, Fagan, Minnich & McKee

(57) ABSTRACT

An integrated respiratory monitor and imaging device apparatus (10) is provided. The apparatus is useful for establishing pre-operative and intra-operative breath hold congruency in patients and for other interventional work. The apparatus (10) includes a respiratory monitor system (12) and an imaging device (14). The respiratory monitor system is adapted to engage a patient and generate a respiratory signal representative of a breath hold level of the patient during a breath hold. The imaging device (14) is adapted to scan the patient during the breath hold and generate a volumetric image data set of the patient. The respiratory sensor and imaging device are operatively connected to associate the respiratory signal representative of the breath hold level of the patient together with the volumetric image data set of the patient. A data storage device (64) is provided for storing a set of respiratory signals in association with a corresponding set of volumetric image data sets in the subject apparatus (10). A scanner gating function is provided to center the image acquisition time at selected points in the respiratory cycle such as at a minimum to minimize motion artifacts in the resultant image.

51 Claims, 10 Drawing Sheets

U.S. PATENT DOCUMENTS

| | | | |
|---|---|---|---|
| 6,298,260 B1 * | 10/2001 | Sontag et al. | 600/413 |
| 6,306,095 B1 * | 10/2001 | Holley et al. | 600/458 |
| 6,597,939 B1 * | 7/2003 | Lampotang et al. | 600/427 |
| 6,937,696 B1 * | 8/2005 | Mostafavi | 378/95 |

FOREIGN PATENT DOCUMENTS

| | | |
|---|---|---|
| EP | 1 055 935 A2 | 11/2000 |
| EP | 1 086 652 A1 | 3/2001 |

* cited by examiner

CT INTEGRATED RESPIRATORY MONITOR

CROSS-REFERENCE TO RELATED APPLICATION

This application claims the benefit of U.S. Provisional Application Ser. No. 60/369,485 filed Apr. 3, 2002.

BACKGROUND OF THE INVENTION

The present invention relates to the art of interactive image-guided surgery and interactive surgical procedures which require patient breath holding or breathing control. It finds particular application in conjunction with planning and implementation stages of minimally invasive stereotactic surgical procedures performed in CT imaging systems using a localization device to orient surgical tools such as biopsy or brachytherapy needles or the like for tissue sampling or planning or placement of objects or instruments within the body of a patient, and will be described with particular reference thereto. It is to be appreciated, however, that the invention is also applicable to a wide range of imaging equipment and techniques, for example ultrasonic and magnetic resonance imaging devices, and to a broad range of minimally invasive surgical procedures including many forms of surgery for placing objects or instruments at precise locations within a patient such as interventional radiology procedures and others.

In certain surgical procedures, there is a need for patient breath holding. Technological advances have enabled multi-detector row CT scanners to acquire high resolution scans over a region during a patient breath hold maneuver within a time period of less than ten seconds. Overall, this has enabled an increased number of patients to hold their breath for the short time period required to complete the scan to minimize motion artifacts. However, the increased Z-axis resolution of these CT scanners is not fully utilized when artifacts arising from respiratory motion are introduced into the image. As can be appreciated, patient respiration can change the position of tissues, targets, and critical structures during CT scanning. Simply, modern scanning apparatus are sensitive to patient motion.

In an attempt to minimize motion artifacts arising from respiration, patient breath holding training has been utilized. However, in spite of a training period, some patients (about 20%) have difficulty either initiating the breath hold when instructed to do so at the start of the scan or have difficulty holding their breath throughout the scan. Images acquired under those circumstances suffer from motion artifacts.

Another problem arising from procedures requiring breath holding is the relative inability to provide pre-operative and intra-operative breath hold congruency. More particularly, breath holds during the pre-operative planning phase and during the intra-operative phase of interventional treatments can vary leading to gross inaccuracy in instrument position or object placement within the patient.

Still further, another shortcoming of prior systems is the inability to completely integrate the patient imaging device/workstation with the patient breath holding detection devices. More particularly, data obtained from breath holding transducers currently available is not associated in any meaningful or useful way with the scanner/workstation displays, user controls, or with the acquired patient image data.

Overall, prior methods and apparatus do not automatically detect breath hold and do not have a means to automatically detect a deviation from a breath hold during a scan. Further, the prior systems are unable to record respiratory parameters together with imaging data such as CT data sets. They are further unable to record information with the imaging data relating to whether breath hold was maintained during a patient scan. Still further, the prior techniques are unable to stop the scanner when the breath hold is deviated and then restart the scanner after reestablishing the breath hold.

There is a need, therefore, to provide an automated, easy-to-use CT integrated respiratory monitoring device and method of using same. Preferably, the CT integrated respiratory monitoring device and method is useful in applications including breath holding during CT scanning, breath hold targeting for pre-operative and intra-operative interventional procedures, and for respiratory gating of imaging scanners.

Further, there is a need to provide a system for determining whether a patient is holding their breath at the start of an imaging scan. The system should be able to alert the technologist if the patient does not maintain the breath hold during the scan and identify images that were acquired while breath hold was not maintained. Preferably, the system provides an intuitive relaxing visual feedback to the patient to help them maintain their breath hold during the scan.

The present invention provides a new and improved CT scanner with integrated respiratory monitoring device and method of using same which overcomes the above-referenced problems and others.

SUMMARY OF THE INVENTION

In accordance with one aspect of the present invention, a system including an integrated respiratory monitor and patient imaging device, and method of using same, are provided. Data representative of a breath hold level of a patient during a scan is associated with a volumetric image data set of the patient generated from said scan.

In accordance with a more detailed aspect of the invention, a method and apparatus for use in breath holding applications during CT scanning is provided.

In accordance with yet another aspect of the invention, a method and apparatus for use in breath hold targeting applications for interventional minimally invasive procedures is provided.

In accordance with yet another aspect of the invention, a method and apparatus for respiratory gating applications in conjunction with patient CT scanning is provided.

In accordance with yet a still further aspect of the invention, a method and apparatus is provided for associating patient imaging data sets with respiratory data recorded during the patient imaging scan. Data representative of the entire respiratory signal during scanning is stored together with the image volume data set.

In accordance with another aspect of the invention, an integrated system is provided for acquiring patent images during free breathing by triggering the scanner at selected phases of the respiratory cycle. In one embodiment, the scanner is gated slightly before the minimum in the respiratory cycle, such that the acquisition of projections is centered on the minimum, thereby minimizing motion artifacts.

The preferred apparatus for associating acquired image data sets with breath holding parameters is an integrated respiratory monitor and imaging device including a respiratory sensor and an imaging device. The respiratory sensor is adapted to engage a patient and generate a respiratory signal representative of a breath hold level of the patient during breath hold maneuvers. The imaging device is adapted to scan the patient during the breath hold and generate a volumetric image data set of the patient. The respiratory sensor and the imaging device are operatively connected to associate the respiratory signal representative of the breath hold level of the patient together with the volumetric image data set of the patient. The respiratory signal is preferably stored as data in a data storage of the imaging device together with the acquired volumetric image data set.

One primary advantage of the invention is the association of respiratory parameters recorded during patient imaging scans together with the patient volumetric image data. In that way, radiologists and interventionists can use the respiratory parameters in determining whether the image of the patient is accurate and in making other medical and technical determinations. The parameters and image data are stored in a memory for later retrieval as needed. The association of the respiratory parameters directly with the image data significantly improves the integrity of the imaging system and thus enhances overall medical treatment of the patient.

Another significant advantage of the invention is that it used to help patients maintain a breath hold during CT scanning. The patient display showing patient breath hold levels is intuitive and relaxing to the patient. Using this system, patients are easily trained for breath holding.

Still yet another advantage of the invention is that selected images are associated with suitable identifiers when breath hold parameters are not maintained. In that way, images with artifacts caused by patient motion due to breathing are not relied upon in making medical determinations because those images are associated with data indicative of poor breath hold performance.

Another advantage of the invention is to provide a system establishing good pre-operative and intra-operative breath hold congruency performance to facilitate interventional procedures and enable patient image comparisons at like breath hold levels.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF THE PREFERRED EMBODIMENTS

Figure 1:
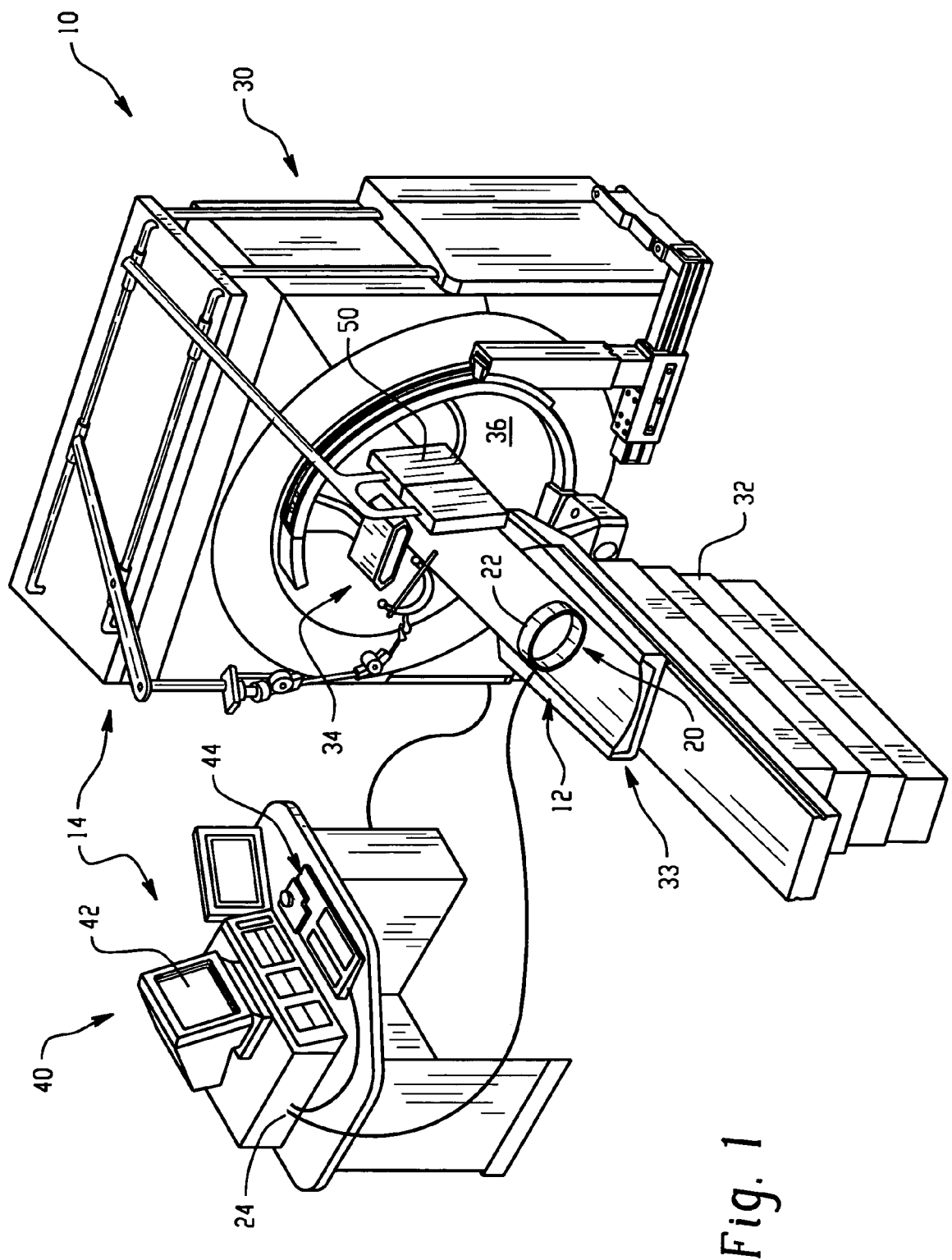
FIG. 1 is a diagrammatic illustration of an integrated CT scanner and respiratory monitoring device according to the preferred embodiment of the invention.

Referring now to the drawings wherein the showings are for purposes of illustrating the preferred embodiments of the invention only and not for purposes of limiting same, with reference first to FIG. 1, an integrated apparatus 10 includes a respiratory monitor system 12 and a CT imaging device 14. The integrated apparatus 10 is particularly well suited for planning and executing minimally invasive surgical procedures for in-vivo placement of instruments and/or objects within a patient during one or more breath holds.

The respiratory monitor system 12 includes a respiratory sensor 20 preferably formed as a belt 22 adapted for attachment around the abdomen or chest of a patient. In its preferred form, the respiratory sensor 20 includes an air bellows sensor and pressure transducer (not shown) for generating a signal corresponding to the displacement of a patient's abdomen during respiration. The respiratory sensor 20 is attached to the imaging device 14 at a suitable electronic connection point 24.

With continued reference to FIG. 1, the preferred imaging device 14 is a volumetric diagnostic CT imaging apparatus 30 as shown. The CT imaging apparatus 30 is disposed in axial alignment with a patient table 32 and support 33 such that a patient or subject on the support surface can be moved into and through a bore 34 of the CT volumetric imager 30. The CT scanner includes an x-ray tube mounted for rotation about a preselected plane. The x-ray tube projects a fan shaped beam of radiation through a ring 36 of radiation translucent material, through the patient support 33, through a region of interest of the patient, and to a ring or arc of radiation detectors disposed opposite the x-ray tube. As the x-ray tube rotates within the plane, a series of data lines are generated, which data lines are reconstructed into at least a slice image using well known techniques by a reconstruction processor included in a control console 40 operatively connected with the CT imager 30.

As is well known in the art, the patient support 33 moves longitudinally as the x-ray tube is rotating around the subject such that a selected volume of the patient is scanned along a spiral path or a series of slices. The position of the x-ray tube is monitored by a rotational position encoder and the longitudinal position of the patient support is monitored by similar position encoders disposed within the table 32. The reconstruction processor reconstructs a volumetric image representation from the generated data lines. The control console 40 includes one or more human readable display devices preferably in the form of an operator monitor 42 and at least one operator input device 44, such as a keyboard, track ball, mouse, or the like. Lastly with reference to FIG. 1, a human readable patient display device 50 is supported from overhead on a track or by other means atop the CT scanner 30. The patient display device can be oriented or moved into selected positions for ready viewing by a patient on the support 33.

Figure 2:
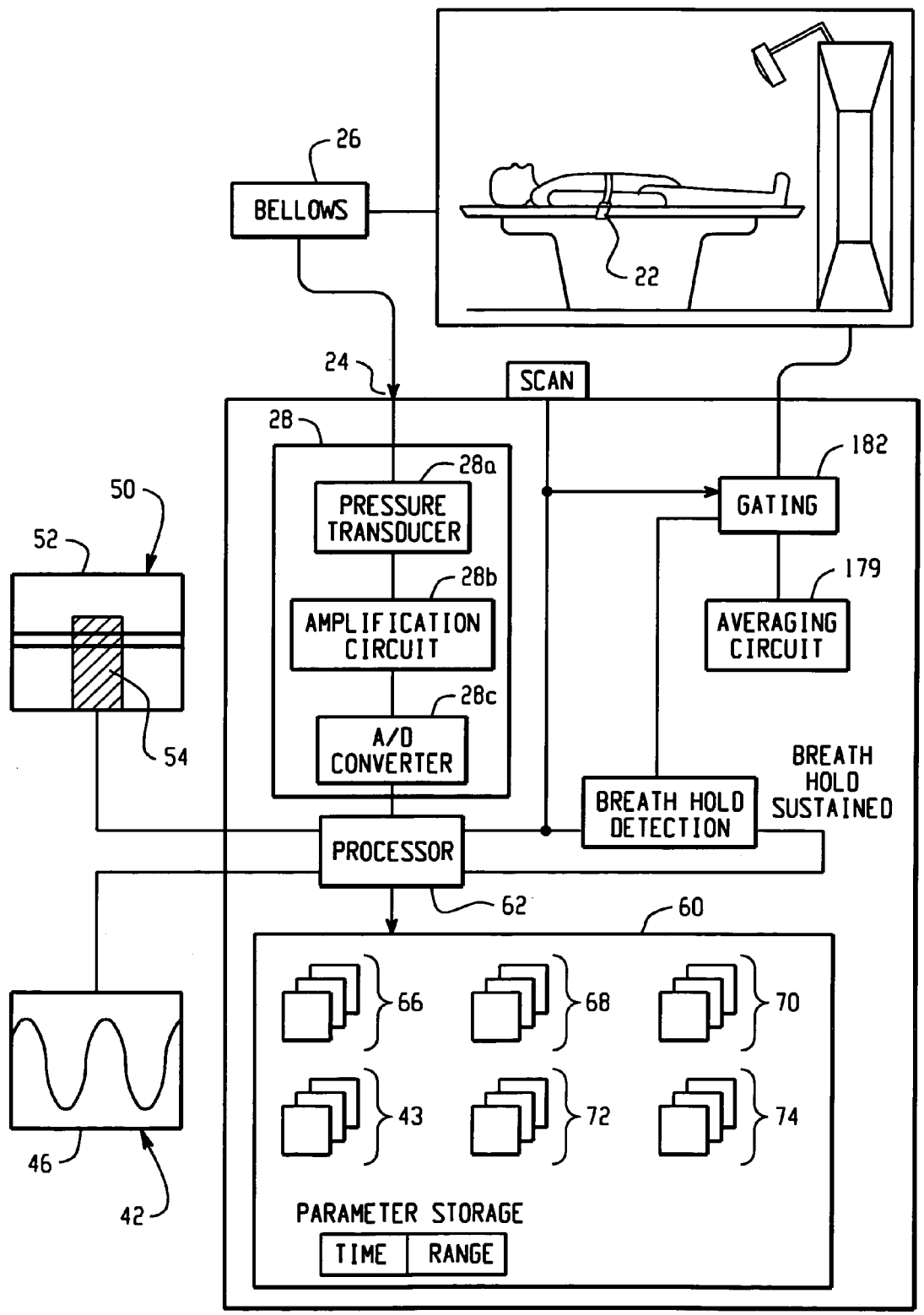
FIG. 2 is a schematic representation of the subject integrated CT scanner and respiratory monitoring apparatus.

FIG. 2 is a schematic representation of the subject CT integrated respiratory monitoring apparatus 10. As illustrated, a processing computer system 60 is operatively connected with each of the components of the subject integrated apparatus 10. More particularly, the computer system 60 is adapted to generate a patient image volume data set 43, an operator's image 46 of a patient breath hold signal on the operator monitor 42 as well as a patient breathing image 52 on the patient display device 50.

As shown, the preferred patient breathing image 52 is visual indicia in the form of a bar graph 54 having a height representative of an inhalation level of the patient on a scale of percentage of vital capacity (% VC). In order to adjust for variations of placement of the sensor belt on the patient, gains and affects are applied based on vital capacity for display purposes. The patient breathing image 52 is in the form of a bar graph 54 to make it easy for patients to relate and coordinate the image with their own physical breathing conditions and breath hold levels. It is to be appreciated that although a bar graph is illustrated, other forms of patient breathing images can be used as well such as, for example, a graduated cylinder, a progress bar, an animated diaphragm, and the like. During a scan, the patient uses the graphic feedback to set and maintain a breath hold. With such a display, a few moments of training prior to the CT scan enables a high percentage of patients to control their breathing in order to accomplish desired breath hold maneuvers.

With continued reference to FIG. 2, the computer system 60 is also operatively connected with the respiratory sensor 20 at the electronic connection point 24. The respiratory sensor 20 includes a belt 22 adapted to be worn across the abdomen or rib cage of a patient as discussed above and an air bellows device 26 as well as a respiratory sensor circuit 28. Preferably, the respiratory sensor circuit 28 includes a pressure transducer 28a responsive to a condition of the air bellows 26 as well as an amplification circuit 28b for amplifying the electrical signal from the pressure sensor to a level suitable for input to an analog to digital converter circuit 28c. The conversion of analog signals from the belt 22 representative of a position of the patient's abdomen to a digital signal for use by the computer system 60 is well known in the art and can be accomplished using any suitable equivalent means.

With yet continued reference to FIG. 2, the computer system 60 includes a processor 62 for executing instructions to control the integrated apparatus 10 in accordance with the present invention. The computer system 60 further includes a memory storage device 64 adapted to store various data and parameters for operating the integrated apparatus 10 including a portion of memory dedicated to storing a plurality of sets of patient volumetric image data 66 in association with patient breath hold level data 68. More particularly, the subject apparatus 10 stores each volumetric patient image data set obtained during a scan together with the patient breath hold level data obtained during the scan in a paired relationship. Alternatively, the breath hold level data can be stored together with the volumetric image data in a designated field or segregated portion of the image data as desired. In addition, for each volumetric patient image data set 66 the computer system 60 stores breath sustained data 70 indicative of whether a patient held his/her breath for a sustained selectable period and within a selectable level/range. The breath hold target period is determined by breath hold period data 72 selectable by the operator. Similarly, the breath hold range target is determined by range data 74 selectable by the operator. Other data or information derived from the respiratory monitor system 12 can be stored in association with the patient volumetric image data as desired. It is further to be appreciated that the interventionist can set the breath hold target as needed based on particular interventional procedures. As examples, the targets can be inhale and hold, exhale and hold or shallow breathe and hold.

Figure 3:
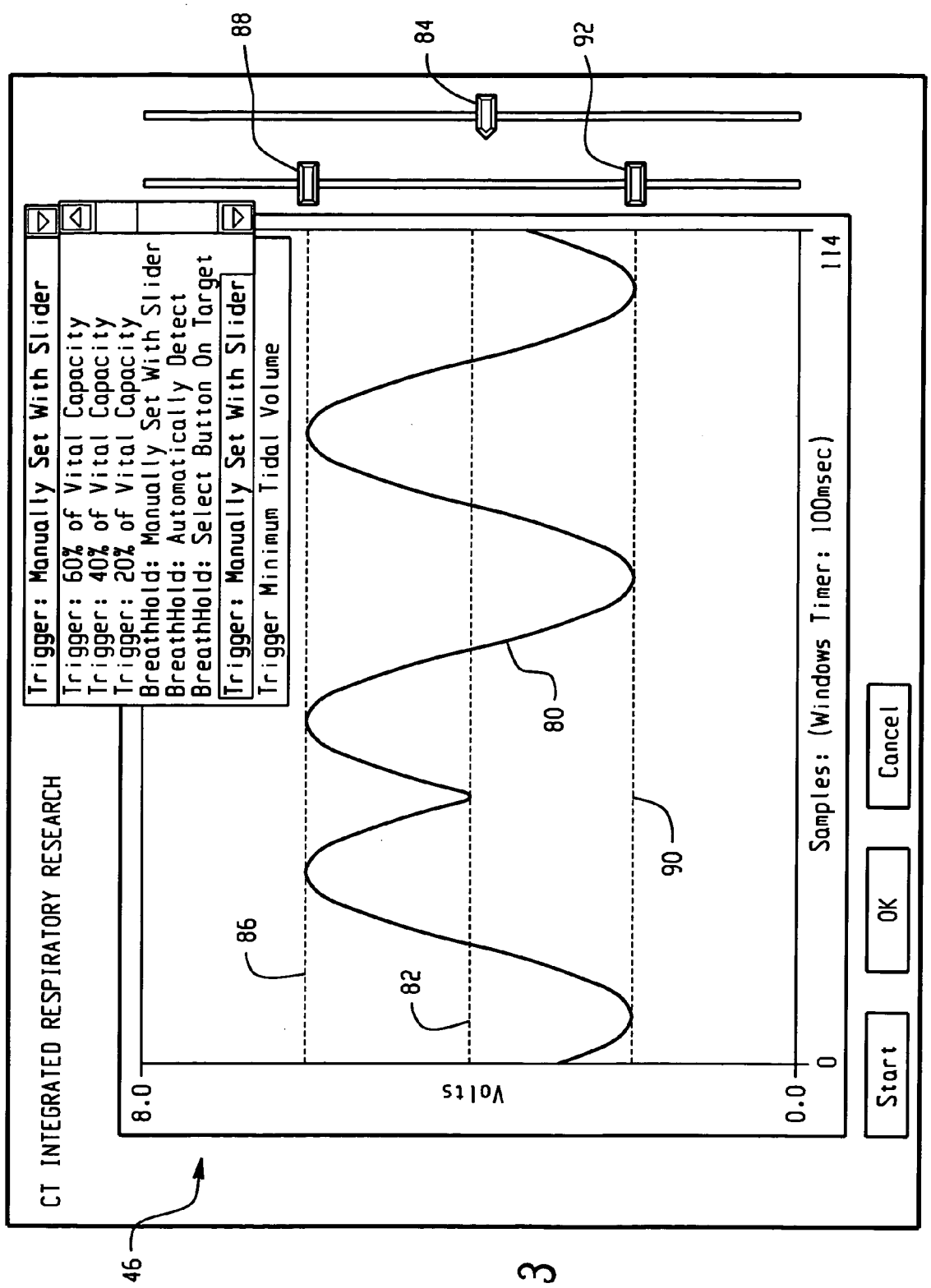
FIG. 3 is a an illustration of a representative operator's image displayed on an operator's monitor in the system of FIG. 1.

FIG. 3 shows a representative operator's image 46 displayed on the operator monitor 42 of the control console 40. The image 46 includes a patient breathing signal or graph 80 shown on a Cartesian coordinate system with time plotted on the abscissa and the patient breathing level signal in volts plotted on the ordinate. The breathing signal 80 is derived from the respiratory sensor 20 of the respiratory monitor system 12 and through the computer system 60 described above. In accordance with the preferred embodiment, a patient target breath hold level 82 is selectable using a target slider button 84 or by selecting preset configuration parameters such as target +/−5% or target +/10%, or the like. Similarly, a breath hold range is set between an upper breath hold level 86 using target slider 88 and a lower breath hold level 90 using target slider 92. This causes data values to be loaded in the breath hold level/range storage 74 discussed above. As shown in the FIGURE, the patient's normal breathing is between the upper and lower breath hold tolerance range respectively. The target sliders can be used to determine the low and high extents of the patient's vital capacity (VC).

Figure 4:
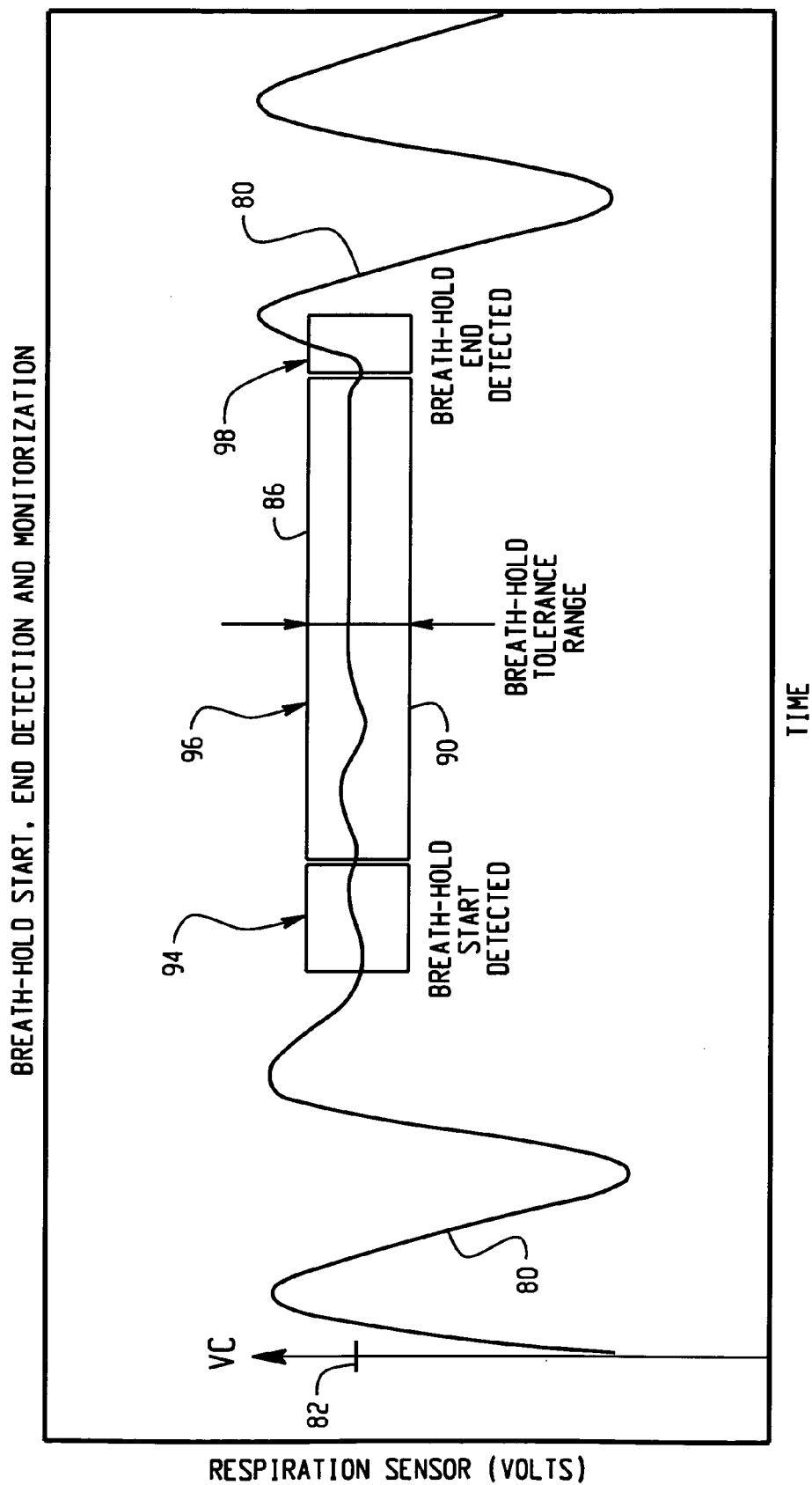
FIG. 4 is a graph showing a display of a patient breathing signal.
Figure 5:
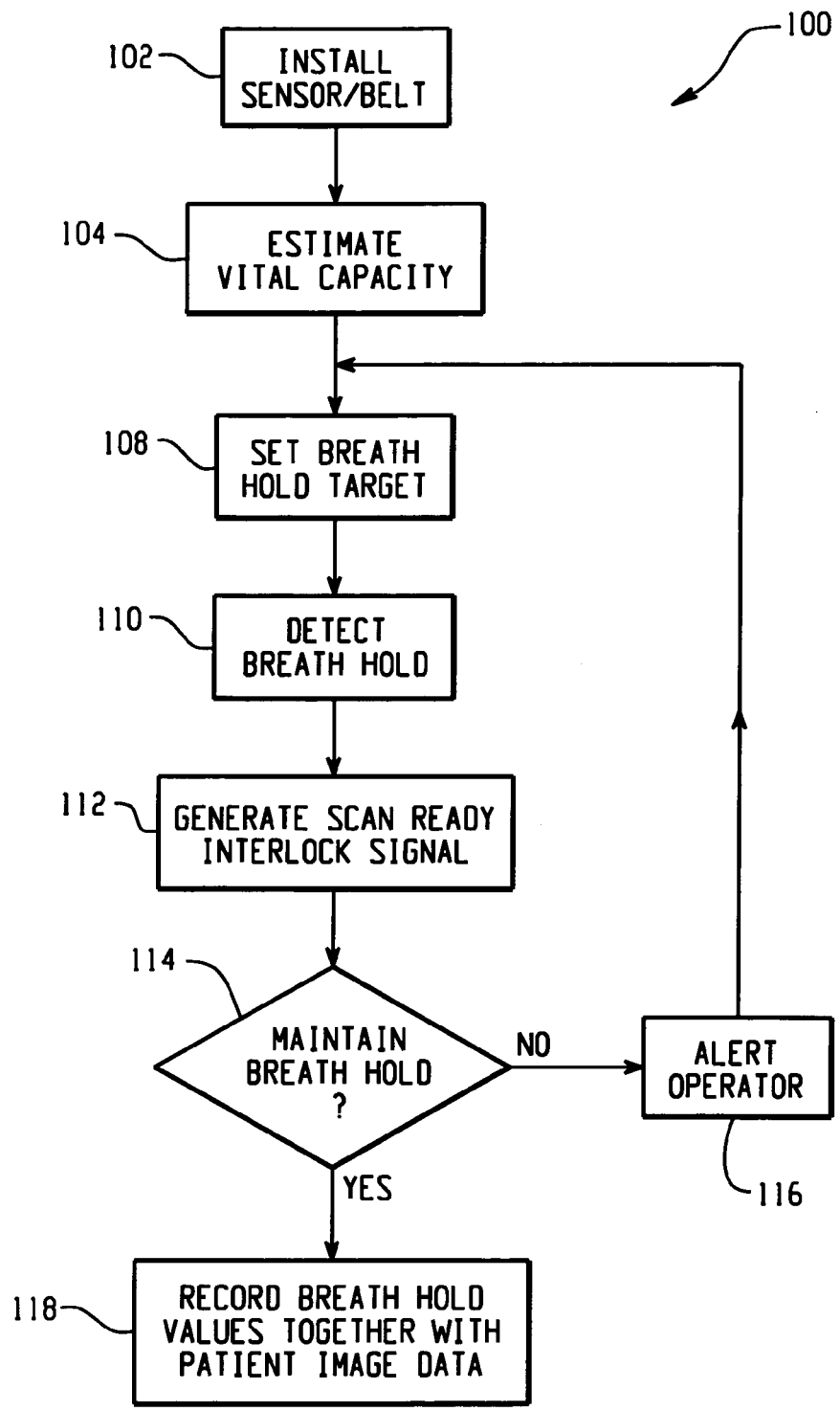
FIG. 5 is a flow chart describing a preferred method of using the system shown in FIG. 1.
Figure 6A:
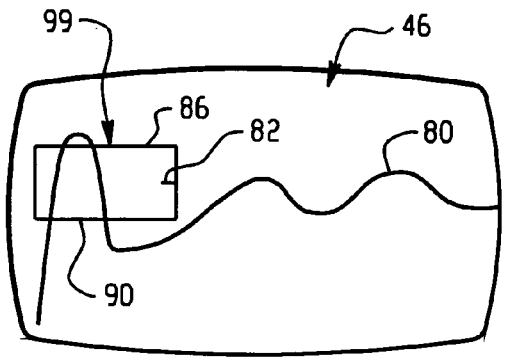
FIGS. 6a–6c show a series of operator display views obtained during practice of the method of FIG. 5.
Figure 6B:
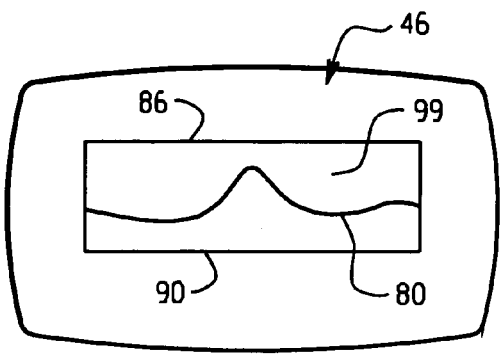

In FIG. 4, the patient's normal breathing is outside of the upper and lower breath hold levels 86, 90, respectively. More particularly, as illustrated by way of example, the breath hold tolerance range is about ¼ of the patient's vital capacity (VC) and the nominal target breath hold level 82 is at about 80% of the patient's vital capacity. As shown, during a first time period 94 the subject integrated apparatus 10 detects a breath hold start based on the breathing signal 80 being within the breath hold tolerance range 86, 90. The breath hold sustained is detected during a second time period 96 set by the operator and stored as the breath sustain period data 72 discussed above. Thereafter, during a third time period 98, a breath hold end is detected when the breathing graph 80 exceeds the upper breath hold level 86.

FIGS. 5, 6a–6c, and 7a–7c will be used to describe a method 100 for acquiring patient images obtained at target breath hold levels in accordance with a preferred embodiment of the present invention. Initially, the respiratory sensor 20 is installed 102 by connecting the belt 22 to the patient's abdomen. At step 104, the interventionist observes patient's breathing levels (FIG. 6a) on the operator's monitor 42 in order to determine a patient's vital breathing capacity. As noted, a patient breathing image 52 is also displayed (FIG. 7a) but in the form of a bar graph 54 on the patient display device 50.

Based upon information obtained in step 104, the interventionist sets a breath hold target level 82 and upper and lower breath hold levels 86, 90 in a manner described above using the control buttons 84, 86, 92 illustrated in FIG. 3. The target breath hold range 99 is illustrated on the operator's image 46 as a rectangular box having a height corresponding to the range. Correspondingly, the breath hold range 99' is illustrated on the patient breathing image 52 as a horizontal bar having a width defined by boundaries 86', 90' corresponding to the target breath hold range 86, 90.

At step 108, the interventionist instructs the patient to target a breath hold condition such that the top edge of the bar graph 54 is positioned within the horizontal bar 99 defining the breath hold tolerance range. The intuitive nature of the bar graph representation of breathing level makes it easy for a patient to maneuver his/her breath hold condition into the target range. At step 110, the computer system 60 of the subject integrated apparatus 10 detects a breath hold condition when the patient's breathing level is within the selected range using the range/level parameter 74 and duration 72 parameters selected by the operator. A scan ready signal is generated at step 112 based upon the detected breath hold.

Figure 7A:
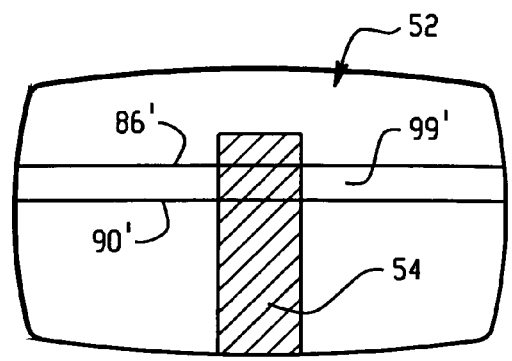
FIGS. 7a–7c are a series of images displayed on the patient monitor during practice of the method of FIG. 5.
Figure 7B:
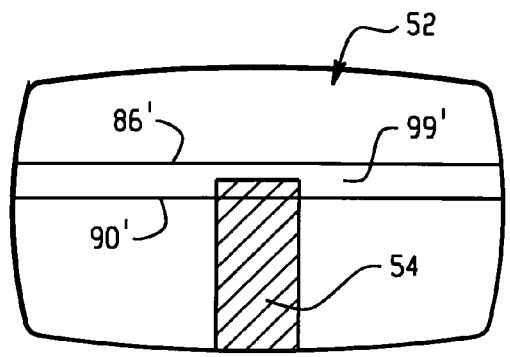
Figure 6C:
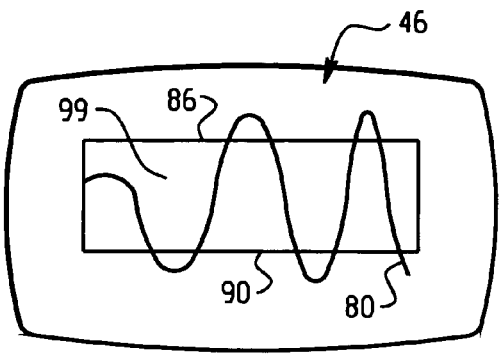
Figure 7C:
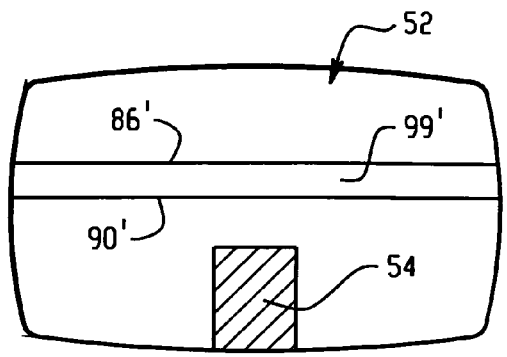
Figure 8:
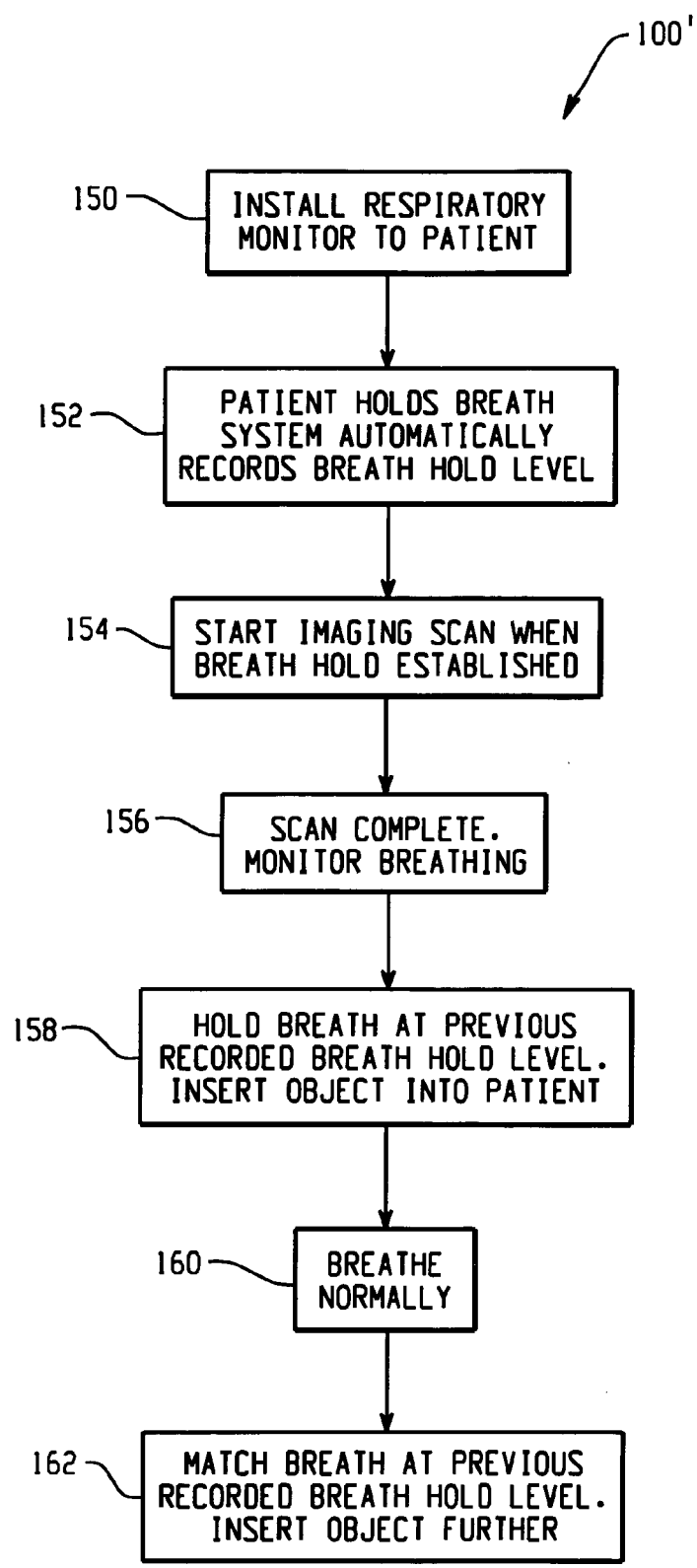
FIG. 8 is a flow chart illustrating a method of using the subject system to provide pre-operative and intra-operative breath hold congruency.

During the patient imaging scan, the operator's display shows the patient's breathing graph 80 together with the range target rectangle 99. Similarly, the patient display of FIG. 7*b* shows the bar graph 54 overlaid on the target range 99. In step 114, the system determines whether the breathing graph 80 either exceeded the upper breath hold level 86 or fell short of the lower breath hold level 99 during the scan. If at any point during the scan the breathing graph 80 fell outside of the defined upper and lower breath hold level boundaries, the operator is alerted at step 116 so that suitable corrective action can be taken such as, for example discarding the obtained image data, reestablishing the target breath hold level and providing a subsequent patient scan.

If the patient successfully held his breath during the scan, the volumetric patient image data generated during the scan is stored in the memory storage device 60 in association with the patient breath hold information including breath hold level data 68 breath hold sustain data 70 breath hold period data 72, and breath hold level/range data 74. It is to be appreciated that the storage of the patient breath hold level data, particularly breath hold level (% VC) data together with the volumetric patient image data is particularly useful for comparison type evaluations such as, for example, in emphysema evaluations where the period between scans can be weeks or months. In those cases, it is critical that the comparison between patient image scans be made at equivalent breath hold datums. In addition, the ability to store patient breath hold level data together with the volumetric patient image data is significant for providing pre-operative and intra-operative breath hold congruency as described below.

Figure 9A:
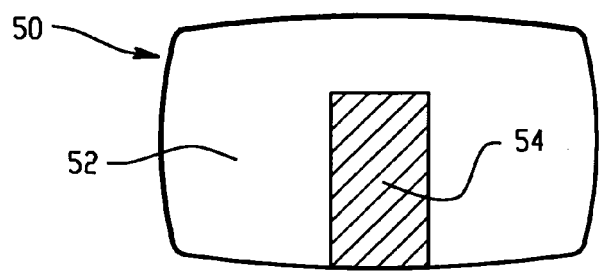
FIGS. 9a–9e illustrate a series of visual displays generated at the patient monitor during practice of the method of FIG. 8.
Figure 9B:
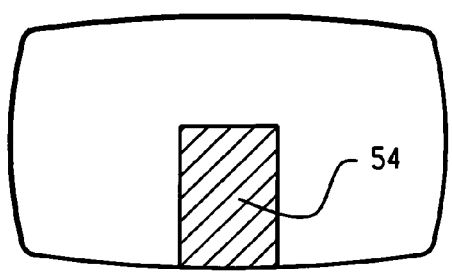

Turning next to FIGS. 8 and 9*a*–9*e*, a method 100' of using the subject integrated apparatus to provide for preoperative the intra-operative breath hold congruency in accordance with another preferred embodiment will be described. Initially, at step 150, the respiratory sensor 20 is connected with the patient by attaching the belt to the abdomen or across the chest. The patient's respiratory function is illustrated as a moving bar graph 54 in the patient breathing image 52 on the patient display device 50 (FIG. 9*a*). Next, in step 152 the patient holds his breath at a selected level. This is illustrated in the bar graph 54 in FIG. 9*b*.

After the computer system 60 determines that a breath hold is established at step 154, the patient breathing image 52 is provided with a range indicia 99'. The imaging device 14 is initiated to start a scan while the patient holds his breath at a physical level in order to maintain the bar graph 54 in the range 99'.

Figure 9C:
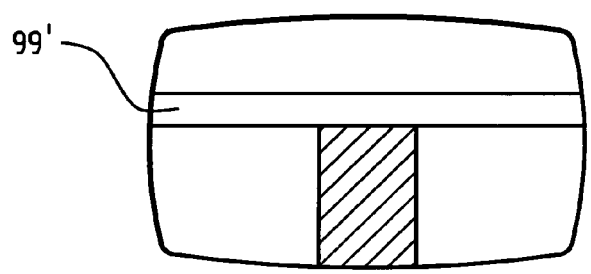
Figure 9D:
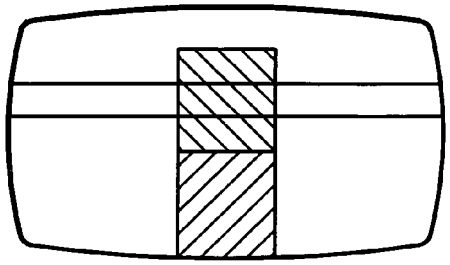
Figure 9E:
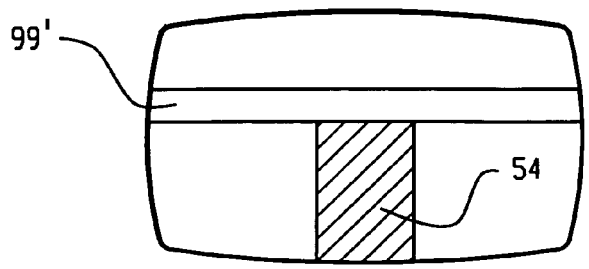

After the scan is completed at step 156, the operator instructs the patient to breathe normally at which time the color of the bar graph 54 in the patient breathing image 52 changes color as the bar graph moves above and below the range 99' (FIG. 9*d*). The changing color provides visual indicia of an out of range breath hold condition which is easily recognizable and intuitive to the patient. Thereafter, the patient and the doctor together monitor normal breathing of the patient.

Next, in step 158, the patient is instructed to sustain the breath hold level used during the patient scanning in step 154. Simply, the patient controls the breathing maneuver in order to cause the top end of the bar graph 54 to lie within the range 99' illustrated on the patient breathing image 52. The patient holds his breath in this manner during which time a needle or other object can be inserted into the patient using standard image guided techniques based on the volumetric patient image data using well known techniques.

Thereafter, in step 160, the patient is allowed to breathe normally so that needle position in the patient can be verified such as by a subsequent scan of the patient using the CT scanner or other device/modality (FIG. 9*d*).

Thereafter, in step 162, the patient is instructed to once again match the breath hold level within the selected range so that the needle can be advanced further into the patient or so that other procedures or steps can be taken at the target patient breath hold level (FIG. 9*c*).

The subject CT integrated respiratory device is also particularly useful in respiratory gating of the scanning function. This involves triggering the CT scanner 14 at selected points in the respiratory cycle while the patient is freely breathing. Clinical applications for respiratory gating include procedures that have a duration or image acquisition period that exceeds the amount of time that a patient can be expected to hold their breath. One example of such application is for imaging a patient for a liver perfusion procedure. The subject respiratory tracking and monitoring device is self-calibrating relative to an estimated value proportional to a patient's vital capacity and allows CT slices to be triggered at optimal points in the patient breathing cycle.

Figure 10:
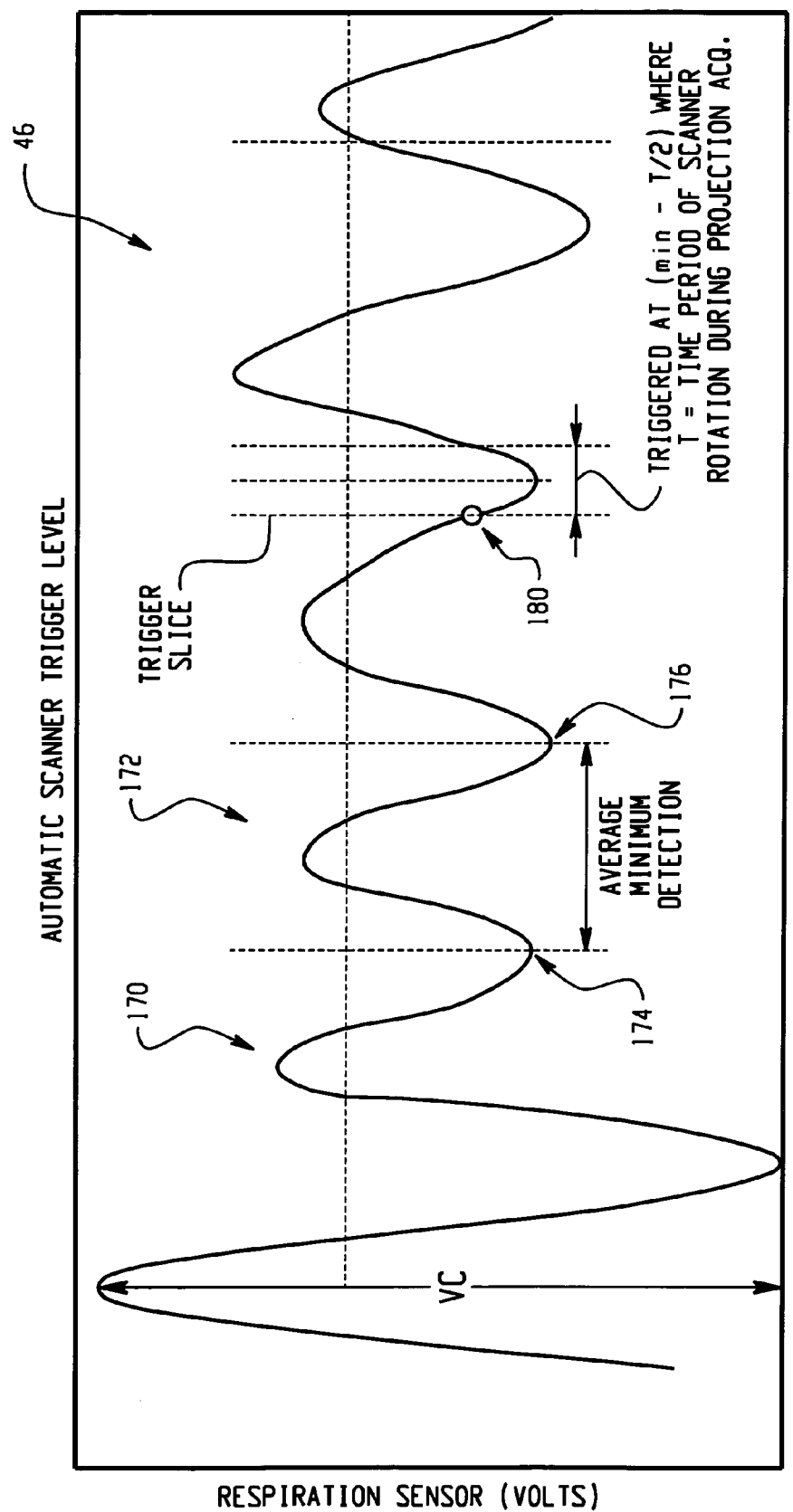
FIG. 10 is a view of a patient breathing signal illustrating use of the subject system to automatically trigger CT scanner operation using a calculated breath hold level; and, FIG. 11 is a schematic illustration of an alternative respiratory sensor for use with the subject system.

As shown in FIG. 10, a patient breathing graph 80 is displayed as an operator's image 46 on an operator monitor 42. For applications that benefit from or require respiratory gating, an embodiment of the invention provides an integrated trigger function to acquire a complete scan based on scanning only at specific points in the respiratory cycle. In this use, the scanner is triggered at selected phases of the respiratory cycle during free breathing. The triggering function adapts to the scanner's image acquisition capabilities. In this description, it is assumed that the scanner requires T seconds to acquire a projection for a slice. T is related to scan speed which decreases with improvements in scanner technology and scan projection angle.

Respiratory motion artifacts are minimized by triggering the scan/slice at the minimum in the respiratory cycle. The signal processing further minimizes motion effects by centering the projection acquisition time interval, T, at a time point estimated for the minimum in the respiratory signal. Essentially, the slice is triggered at T/2 from the anticipated minimum in the respiratory cycle. In an alternate embodiment, triggering based on patient breathing a fixed percentage of vital capacity is provided. Preferably, the respiratory signal (non-breath hold) is stored in association with the volumetric data set. It is to be appreciated that although gating at the minimum in the respiratory cycle is described, the invention can be used at any selected point in the respiratory cycle.

With continued reference to the patient breathing graph of FIG. 10, a first period 170 of the breathing graph 80 is used to determine the patient's vital capacity VC. Thereafter, in a second period 172 the computer processing system 60 determines an average minimum lower breath hold levels using a standard averaging technique. More particularly, a first minimum lower breath hold level 174 is found followed by a second lower minimum breath hold level 176. Based on the average minimum lower breath level determined by an averaging circuit 179 of the computer system 60, and together with information regarding the expected duration of the patient scan, a scan trigger point 180 is determined according to time=(min.−T/2), where min. is the predicted time for the next minimum breath hold level calculated by the processor 60 and where T equals time period of scanner rotation during projection acquisition. The image slice is triggered in the imaging device 14 by a gating circuit 182 of the computer system 60 at a start point 180 so that about half of the image data is acquired on a patient exhale before a minimum lower breath level and the remaining portion of the image data is acquired on a patient inhale after the minimum lower breath level.

It is to be appreciated that the present system is useful for automatic scanner triggering at any point in the respiratory cycle based upon patient free breathing graph signals inputted into a gating or trigger circuit. As an example, some procedures may require imaging at a maximum point in the breathing cycle and others in the middle range of the cycle. The averaging circuit 179 calculates a predicted time (min. in the above equation) of the next breathing cycle crossing of the selected point. Thereafter, the scan trigger point is calculated as described above, time=(min.−T/2).

Figure 11:
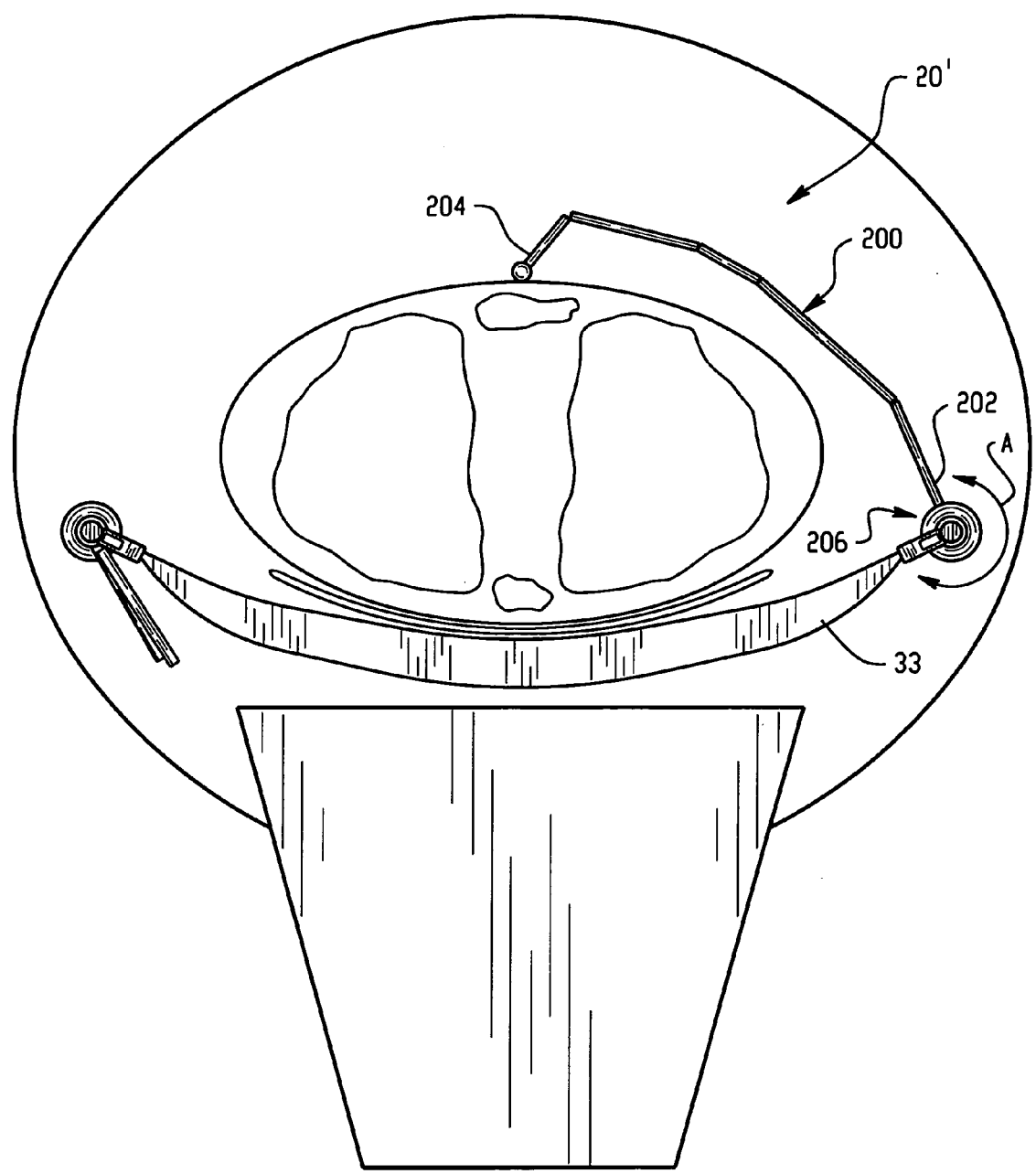

With reference next to FIG. 11, an alternative respiratory sensor 20' is illustrated. As shown there, a sensing device 200 is attached on a first end 202 to the patient support 33 of the patient table 32. The device is preferably telescopic and includes a distal end 204 adapted to contact the abdomen of the patient disposed on the patient support. A shaft encoded rotational joint 206 is provided between the distal end 202 of the device and the patient support so that the position of the distal end can be accurately determined relative to the first end. In that way, motion of the patient is measured on a relative basis during the patient respiratory cycle. More particularly, as the patient breathes, the respiratory sensor 20' rotates in a direction A noted in the FIGURE. Preferably, the shaft encoded rotational joint is a high resolution optical encoder such as one providing 9600 ticks or counts per rotation to resolve the respiratory motion of the patient.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. An apparatus comprising:
    a respiratory sensor adapted to generate a respiratory signal representative of breath hold levels of a patient during a breath hold;
    an imaging device operatively connected with said respiratory sensor and configured to scan the patient during said breath hold and generate a volumetric image data set of the patient, the imaging device being programmed to record said volumetric image volume data set of the patient and said respiratory signal representative of the breath hold levels of the patent taken at a plurality of points in time during said breath hold; and,
    a breath hold determining circuit receiving said respiratory signal and generating a breath hold sustained signal indicating that said respiratory signal remained within a predetermined range during a predetermined time period, the breath hold sustained signal being associated in said apparatus with said volumetric image data set of the patient.

2. The apparatus according to claim 1 further including:
    a human readable patient display device observable by the patient for displaying visual indicia of said breath hold levels.

3. The apparatus according to claim 2 wherein said visual indicia is an animated representation of a physiological structure of said patient.

4. The apparatus according to claim 2 wherein said visual indicia is a bar graph.

5. The apparatus according to claim 1 further including:
    a data storage device for storing said volumetric image data set and said data representative of the respiratory signal.

6. The apparatus according to claim 1 further including:
    a human readable operator display device observable by an operator of said integrated apparatus for displaying visual indicia of said respiratory signal during said breath hold together with an image of the patient developed from said volumetric image data set based on said volumetric image data set.

7. The apparatus according to claim 6 wherein said visual indicia is a graphical display of said respiratory signal on said operator display device.

8. The apparatus according to claim 1 wherein said breath hold determining circuit is adapted to receive said respiratory signal and generate a breath hold interlock signal when a level of said respiratory signal is within a predetermined range for a said predetermined time period.

9. The apparatus according to claim 8 further including a parameter storage, wherein:
    said predetermined range is selectable by an operator of the apparatus based on a percentage of patient vital capacity values set in said parameter storage of the apparatus; and,
    said predetermined time period is selectable by the operator of the apparatus by setting time values in said parameter storage.

10. The apparatus according to claim 8 wherein said predetermined range is 5% vital capacity VC of said patient and said predetermined time period is 2–4 seconds.

11. The apparatus according to claim 8 further including:
    a gating circuit operatively associated with said imaging device and responsive to said breath hold interlock signal to initiate said scan of said patient.

12. The apparatus according to claim 11 wherein:
    the apparatus includes a first input for use by an operator of the apparatus to selectively request initiation of a scan of the patient; and,
    the gating circuit is responsive to said first input to initiate said scan only in a presence of said breath hold interlock signal.

13. The apparatus according to claim 8 further including a visual breath hold interlock display to provide an operator of the apparatus with visual indicia that the patient has sustained a breath hold for said predetermined time period at a level within said predetermined range.

14. The apparatus according to claim 1 wherein the respiratory sensor and the imaging device are operatively connected to record substantially the entire respiratory signal during said breath hold.

15. The apparatus according to claim 8 wherein:
said breath hold determining circuit is adapted to change a logical level of said breath hold interlock signal when a level of said respiratory signal is outside of said predetermined range; and,
said imaging device is adapted to interrupt said scan of the patient in response to said change in said logical level of said breath hold interlock signal.

16. The apparatus according to claim 15 wherein:
said imaging device is adapted to resume said scan of the patient in response to a further change in logical level of said breath hold interlock signal.

17. The apparatus according to claim 8 wherein:
said breath hold determining circuit is adapted to change a logical level of said breath hold interlock signal when a level of said respiratory signal is outside of said predetermined range; and,
said imaging device is adapted to associate indicia of said change in said logical level of said breath hold interlock signal together with said volumetric image data set of the patient.

18. The apparatus according to claim 1 wherein the respiratory sensor includes a belt worn across the abdomen or chest of the patient, the belt generating said respiratory signal in response to motion of said patient during breathing.

19. The apparatus according to claim 1 wherein the respiratory sensor includes a probe member adapted on a first end to contact the abdomen or chest of the patient and adapted on a second end for operative attachment with said imaging device, the probe member generating said respiratory signal in response to motion of said patient relative to said imaging device during breathing.

20. The apparatus according to claim 1 wherein: the respiratory sensor and the imaging device are operatively connected to record the respiratory signal taken at said plurality of points in time during said breath hold together with the volumetric image volume data set in a paired relationship.

21. The apparatus according to claim 20 wherein:
the respiratory sensor and the imaging device are operatively connected to record substantially the entire respiratory signal during said breath hold and said volumetric image volume data set in said paired relationship.

22. The apparatus according to claim 1 wherein:
the respiratory sensor and the imaging device are operatively connected to record said respiratory signal taken at said plurality of points of time during substantially the entire breath hold.

23. An apparatus for establishing pre-operative and intra-operative breath hold congruency in patients, the apparatus comprising:
a respiratory sensor generating a first respiratory signal representative of pre-operative breath hold levels of a patient during a pre-operative breath hold and a second respiratory signal representative of intra-operative breath hold levels of the patient during an intra-operative breath hold;
an imaging device operatively connected with said respiratory sensor and configured to scan the patient during said pre-operative breath hold and generate a pre-operative volumetric image data set of the patient, the imaging device being programmed to associate said first respiratory signal representative of the pre-operative breath hold levels of the patient obtained a plurality of times during said breath hold together with said pre-operative volumetric image data set of the patient;
a data storage device for storing first data representative of the first respiratory signal obtained said plurality of times during said breath hold in association with the pre-operative volumetric image data set;
a breath hold determining circuit receiving said first respiratory signal and generating a breath hold interlock signal when a level of said first respiratory signal is within a predetermined range for a predetermined time period, the breath hold determining circuit being adapted to generate a breath hold sustained signal after said predetermined time period indicating that said respiratory signal remained within said predetermined range during said predetermined time period, the breath hold sustained signal being associated in said apparatus with said pre-operative volumetric image data set of the patient; and,
a human readable display device observable by the patient for displaying first visual indicia of said pre-operative breath hold levels based on said first data from said data storage device, together with second visual indicia of said intra-operative breath hold levels generated by said respiratory sensor.

24. The apparatus according to claim 23 wherein:
said human readable patient display device displays said first visible indicia in a non-moving fashion as a target for said patient, and displays said second visual indicia and a moving image representative of said intra-operative breath hold levels of the patient.

25. The apparatus according to claim 23 wherein said data storage device is adapted to store said first data representative of first respiratory signal and said pre-operative volumetric image data set in a pair relationship.

26. The apparatus according to claim 23 wherein the respiratory sensor and the image device are operatively connected to associate the first respiratory signal representative of the pre-operative breath hold level of the patient obtained a plurality of times substantially during said entire breath hold.

27. An apparatus comprising:
a respiratory sensor configured to generate a respiratory signal representative of a plurality of points of a respiratory cycle of a patient during normal breathing;
an imaging device configured to scan the patient during said normal breathing and generate a volumetric image data set of the patient, the imaging device having a characteristic projection acquisition time interval T and being responsive to a trigger signal to initiate said scan of said patient during said normal breathing; and,
a processor programmed to calculate an average minimum of said respiratory signal and estimate a time MIN of a next occurrence of said calculated average minimum, the processor generating said trigger signal at a time in said respiratory cycle MIN−T/2 to substantially center said projection acquisition time interval about said average minimum of said respiratory cycle to minimize motion artifacts in said volumetric image data set.

28. An apparatus comprising:
a respiratory sensor configured to generate a respiratory signal representative of breath hold levels of a patient during a breath hold;
an imaging device configured to scan the patient during said breath hold and generate a volumetric image data set of the patient, the imaging device being programmed to store data of said respiratory signal representative of the breath hold levels of the patent taken a plurality of times during said breath hold with said volumetric image data set of the patient ; and, a breath hold determining circuit receiving said respiratory signal and generating a breath hold sustained signal indicating that said respiratory signal remained within a predetermined range during a predetermined time period, the breath hold sustained signal being associated in said apparatus with said volumetric image data set of the patient.

29. The apparatus according to claim 28 further including:
a human readable patient display device observable by the patient for displaying visual indicia of said breath hold levels.

30. The apparatus according to claim 29 wherein said visual indicia is an animated representation of a physiological structure of said patient.

31. The apparatus according to claim 29 wherein said visual indicia is a bar graph.

32. The apparatus according to claim 28 further including:
a data storage device for storing said volumetric image data set paired with said data of the respiratory signal.

33. The apparatus according to claim 28 further including:
a human readable operator display device observable by an operator of said integrated apparatus for displaying visual indicia of said respiratory signal during said breath hold together with an image of the patient developed from said volumetric image data set based on said volumetric image data set.

34. The apparatus according to claim 33 wherein said visual indicia is a graphical display of said respiratory signal on said operator display device.

35. The apparatus according to claim 28 wherein said breath hold determining circuit is adapted to receive said respiratory signal and generate a breath hold interlock signal when a level of said respiratory signal is within said predetermined range for said predetermined time period.

36. The apparatus according to claim 35 further including a parameter storage, wherein:
said predetermined range is selectable by an operator of the integrated apparatus based on a percentage of patient vital capacity values set in said parameter storage of the apparatus; and,
said predetermined time period is selectable by the operator of the integrated apparatus by setting time values in said parameter storage.

37. The apparatus according to claim 35 wherein said predetermined range is 5% vital capacity VC of said patient and said predetermined time period is 2–4 seconds.

38. The apparatus according to claim 35 further including:
a gating circuit operatively associated with said imaging device and responsive to said breath hold interlock signal to initiate said scan of said patient.

39. The apparatus according to claim 38 wherein:
the apparatus includes a first input for use by an operator of the apparatus to selectively request initiation of a scan of the patient; and,
the gating circuit is responsive to said first input to initiate said scan only in a presence of said breath hold interlock signal.

40. The apparatus according to claim 35 further including a visual breath hold interlock display to provide an operator of the apparatus with visual indicia that the patient has sustained a breath hold for said predetermined time period at a level within said predetermined range.

41. The apparatus according to claim 35 wherein:
said breath hold determining circuit is adapted to change the logical level of said breath hold interlock signal when a level of said respiratory signal is outside of said predetermined range; and,
said imaging device is adapted to interrupt said scan of the patient in response to said change in logical level of said breath hold interlock signal.

42. The apparatus according to claim 41 wherein:
said imaging device is adapted to resume said scan of the patient in response to a further change in logical level of said breath hold interlock signal.

43. The apparatus according to claim 35 wherein:
said breath hold determining circuit is adapted to change the logical level of said breath hold interlock signal when a level of said respiratory signal is outside of said predetermined range; and,
said imaging device is adapted to associate indicia of said change in logical level of said breath hold interlock signal together with said volumetric image data set of the patient.

44. The apparatus according to claim 28 wherein the respiratory sensor includes a belt worn across the abdomen or chest of the patient, the belt generating said respiratory signal in response to motion of said patient during breathing.

45. The apparatus according to claim 28 wherein the respiratory sensor includes a probe member adapted on a first end to contact the abdomen or chest of the patient and adapted on a second end for operative attachment to said imaging device, the probe member generating said respiratory signal in response to motion of said patient relative to said imaging device during breathing.

46. The apparatus according to claim 28 wherein the respiratory sensor and the imaging device are operatively connected to store data of the respiratory signal representative of the breath hold level of the patient taken a plurality of times during the entire breath hold together with the volumetric image data set of the patient.

47. An apparatus comprising:
a respiratory sensor configured to generate respiratory signals representative of breath hold levels of a patient at a plurality of times during a breath hold;
an imaging device programmed to scan the patient during said breath hold generate a volumetric image data set of the patient, and store: i) said volumetric image data set of the patient and ii) said respiratory signals representative of said breath hold levels of the patient at said plurality of times during said breath; and,
a breath hold determining circuit receiving said respiratory signals and generating a breath hold sustained signal indicating that said respiratory signals remained within a predetermined range during a predetermined time period, the breath hold sustained signal being associated in said apparatus with said volumetric image data set of the patient.

48. The apparatus according to claim 47 wherein said breath hold determining circuit is adapted to generate a breath hold interlock signal when a level of said respiratory signals is within said predetermined range for a predetermined time period, and wherein said breath hold determining circuit is adapted to change a logical level of said breath hold interlock signal when a level of said respiratory signals is outside of said predetermined range, said imaging device is adapted to interrupt said scan of the patient in response to said change in said logical level of said breath hold interlock signal, and said imaging device is adapted to resume said scan of the patient in response to a further change in logical level of said breath hold interlock signal.

49. The apparatus according to claim 47 wherein the respiratory sensor includes a one of:

a belt worn across the abdomen or chest of the patient, the belt generating said respiratory signal in response to motion of said patient during breathing; and a probe member adapted on a first end to contact the abdomen or chest of the patient and adapted on a second end for operative attachment to said imaging device, the probe member generating said respiratory signal in response to motion of said patient relative to said imaging device during breathing.

50. The apparatus according to claim 47 further including:

a data storage storing said respiratory signals and said volumetric image data set of the patient in a paired relationship.

51. The apparatus according to claim 47 wherein the respiratory sensor is adapted to generate said respiratory signals as a plurality of breath hold level data of the patient during substantially the entire breath hold.

* * * * *